United States Patent [19]

Ohlsson

[11] Patent Number: 4,478,350

[45] Date of Patent: Oct. 23, 1984

[54] SPHERICAL CONTAINER OR CHAMBER

[75] Inventor: Johnny Ohlsson, Karlskoga, Sweden

[73] Assignee: Aktiebolaget Bofors, Bofors, Sweden

[21] Appl. No.: 301,344

[22] Filed: Sep. 11, 1981

[30] Foreign Application Priority Data

Sep. 26, 1980 [SE] Sweden .............................. 8006726

[51] Int. Cl.³ ...................... B65D 90/02; B65D 81/02
[52] U.S. Cl. ..................................... 220/436; 109/71;
109/72; 109/1 S; 150/52 H; 220/298
[58] Field of Search ..................... 86/1 B; 220/244, 3,
220/900, 436, 298, 444, 435; 150/52 H; 109/1 S,
71, 72, 74, 59 T; 428/911, 912

[56] References Cited

U.S. PATENT DOCUMENTS

| | | | |
|---|---|---|---|
| 853,825 | 5/1907 | Pascoe | 109/72 |
| 1,144,683 | 6/1915 | Barder | 220/298 |
| 1,197,702 | 9/1916 | Williams | 109/72 |
| 1,603,903 | 10/1926 | Church | 220/298 |
| 2,800,243 | 7/1957 | Ondrejka | 220/444 |
| 3,207,352 | 9/1965 | Reinhart, Jr. | 220/3 |
| 3,301,041 | 1/1967 | Mueller | 86/1 B |
| 3,345,245 | 10/1967 | Hanusa | 206/524 X |
| 3,598,275 | 8/1971 | Francois | 220/444 |
| 3,764,035 | 10/1973 | Silverman | 220/900 X |
| 3,786,956 | 1/1974 | Tabor | 86/1 B X |
| 3,820,435 | 6/1974 | Rogers et al. | 86/1 B |
| 3,871,521 | 3/1975 | Szatkowski | 206/524 |
| 4,100,860 | 7/1978 | Gablin et al. | 220/444 |
| 4,187,758 | 2/1980 | Petty | 109/74 |
| 4,432,285 | 2/1984 | Boyars et al. | 220/468 |

FOREIGN PATENT DOCUMENTS 2041178 9/1980 United Kingdom .................. 86/1 B Primary Examiner—Stephen Marcus
Assistant Examiner—Robert Petrik
Attorney, Agent, or Firm—Pollock, Vande Sande & Priddy

[57] ABSTRACT

The invention deals with a spherical or almost spherical chamber or container 1 which can seal in pressure and splinters produced by explosion, deflagration or detonation of explosive substances. The chamber is constructed with an outer structural shell 2, an inner splinter protection layer 3 and an intermediate shock absorbant layer 4. Openings cut in the chamber wall are provided with equally strong outlets or are sealed with equally strong doors constructed after the same principles as the chamber.

5 Claims, 6 Drawing Figures

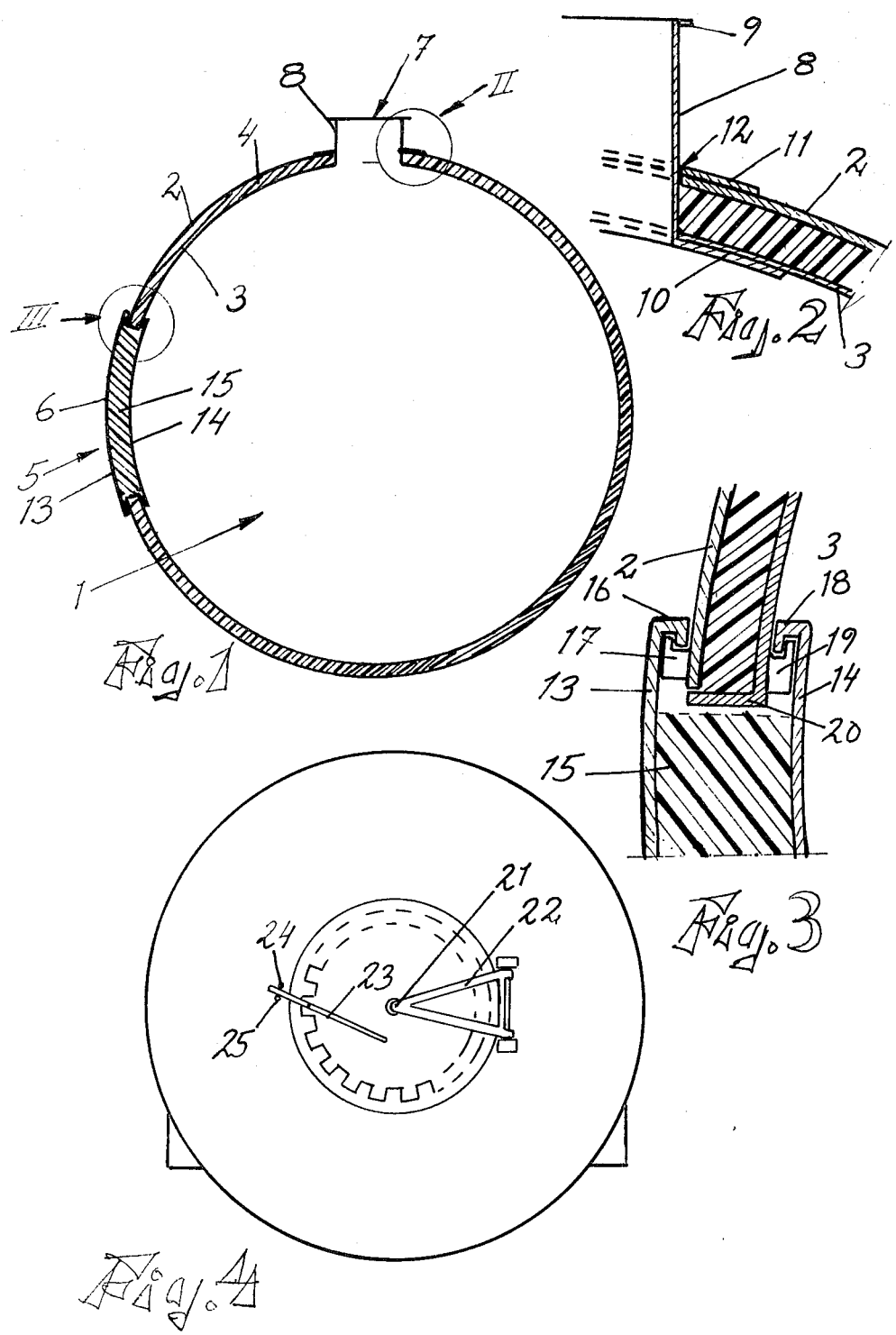

SPHERICAL CONTAINER OR CHAMBER

FIELD OF THE INVENTION

This invention relates to a spherical or almost spherical container or chamber which can seal in pressure and splinters produced by explosion, deflagration, or detonation of explosive substances.

The container or chamber as described by the invention is consequently intended to protect the surroundings by sealing in, for example, especially critical stages of manufacture in processes involving explosive materials. It can even be used as a store for explosive materials or as a laboratory bunker for testing powder and explosive materials.

BACKGROUND ART

Previously, concrete bunkers have almost without exception been utilised for the equivalent purposes. These have in addition often been located under ground, and in those cases where this has not been possible, the entire plant has been surrounded by a safety wall while at the same time the critical part of the plant has been kept as open as possible in order to hold to a minimum the damge caused by a possible explosion.

DISCLOSURE OF THE INVENTION

Compared with these earlier bunker types, the device embodying the present invention is characterised by its adaptable design and relatively low weight. This makes it possible to utilise the chamber in question for the purposes of safety at one or several critical points in an otherwise safe process where the height and location of the chamber must be determined by the general construction of the process plant. A further advantage is that the chamber can be easily adapted to suit differing explosion forces. Also it can be manufactured in various sizes as its design is such that its resistance to explosive forces of varying strengths can be calculated and controlled with great accuracy by the use of mathematical models.

Another advantage with the chamber embodying the present invention is that it is so formed that it can be manufactured complete in the workshop and then in its finished form be transported to and fitted on its site of operation. In this way several different chambers can, if it is so wished, be fitted above or alongside each other.

The chamber embodying the present invention is of a triple-layer construction comprising of an outer structural shell, an intermediate shock absorbent layer, and an inner splinter protection layer in the form of an inner concentric shell integrated with the outer shell. Both the outer structural shell and the inner splinter protection shell are suitably manufactured from steel plate whose dimensions are determined with regard to the prescribed stresses, while the shock absorbant layer preferably comprises a material with completely different qualities as regards the transmission of mechanical vibrations, such as a suitable plastic material. Among the considerations underlying the design of a chamber embodying the present invention is the utilisation of previously derived mathematical models for the calculation of the tensile strength of the shells, individually and collectively. In this way it is even possible to check how the vibrations generated by the internal overpressure created by an explosion transmit themselves through the chamber wall. The chamber is consequently characterised by the fact that the inner shell protects against splinters, the outer shell ensures that the chamber can withstand deflagration or the increase in pressure created by detonation, while the intermediate shock absorbent layer shall be so dimensioned that the vibrations generated in the outer and inner shells never come in phase thereby enabling them to attain critical values. This means therefore that the outer and inner shells may not be metallically connected to each other in such a way that the connection allows critical vibrations to occur in the shells.

Also included in the invention is the fact that all openings in the chamber wall together with those doors or lids intended to seal these openings must made equally as strong as the chamber walls and at the same time be so formed that they do not alter the vibratory pattern for the outer shell and the splinter protection. The doors have therefore been given a special form, and for that reason an adapted wall entry and locking.

Those details are so formed that they do not to any great degree disturb the vibratory pattern between the chamber outer and inner shells.

BRIEF DESCRIPTION OF THE DRAWINGS

The device as described by the invention is defined in more detail in the patent claims which follow. It will now be further described in association with the enclosed Figures.

Of these,

FIG. 1 shows a section through a spherical chamber according to the invention, while FIGS. 2 and 3 show the encircled details II and III in FIG. 1 on a larger scale.

FIG. 4 shows a side projection of a spherical chamber embodying the invention, while

BEST MODE FOR CARRYING OUT THE INVENTION

Figure 5:
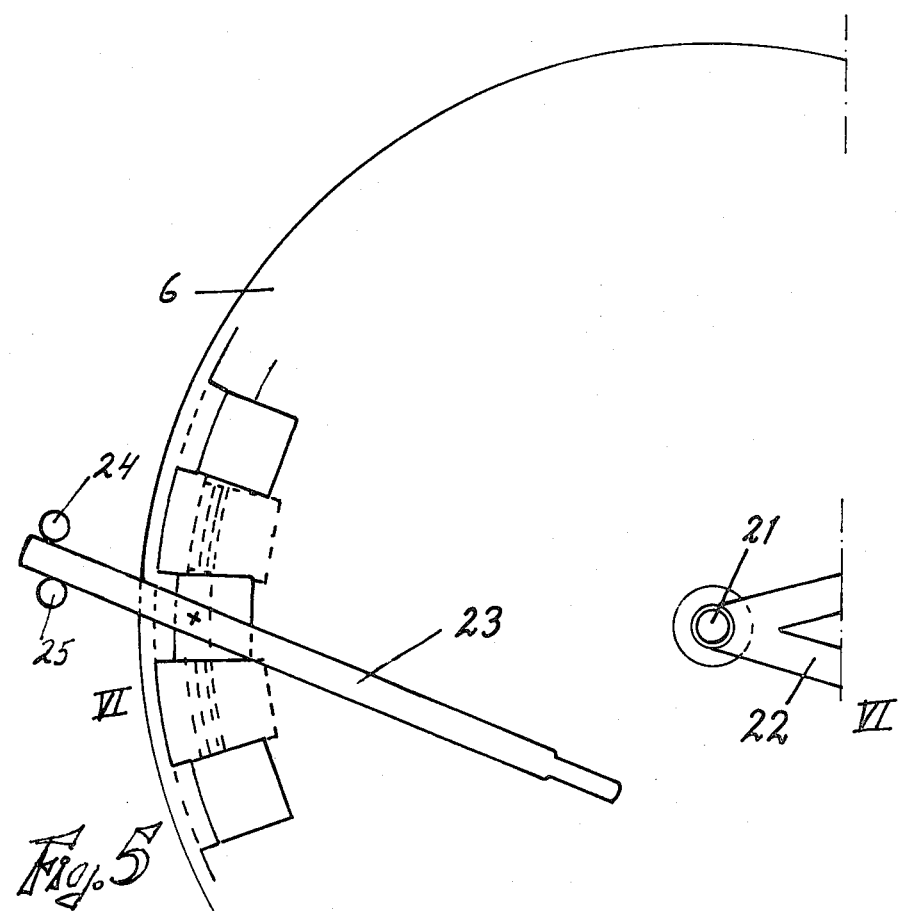
FIG. 5 shows a larger scale detailed drawing of parts of the chamber door together with the immediately surrounding section of the chamber wall. All of the identical periphically arranged, door locking catches are not shown in FIGS. 4 and 5.

The spherical chamber 1 shown in FIG. 1 comprises an outer structural layer 2 preferably made of steel, an inner splinter protection layer 3 likewise preferably made of steel plate, and an intermediate shock absorbent layer 4 preferably made from a suitable plastic material. In the wall of the sphere there is a circular door opening 5 which is closed by a convex circular door 6, and an upper connection opening 7 which is terminated by an outlet pipe 8 fitted with a connection flange 9.

Figure 6:
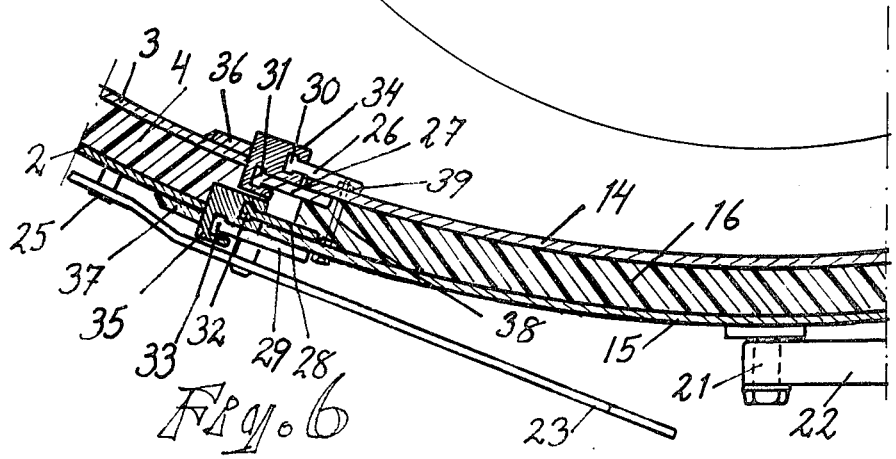
FIG. 6 shows the section VI—VI in FIG. 5.

As can be seen in the detail in FIG. 2, the outlet pipe 8 is directly connected to the inner splinter protection layer 3. Around the opening 7 layer 3 is reinforced with a collar 10. Even the outer structural layer 2 is fitted with a reinforcement collar 11 around the opening 7. Collars 11 is not, however, directly connected to the outlet pipe 8, but between them there is instead a very fine gap or clearance 12. The door 6 also comprises an outer structural layer 13, an inner splinter protection layer 14, and an intermediate shock absorbant layer 15 as shown in FIG. 5. The door is constructed so as to be equally strong as the spherical chamber in general. How the door, in principle, is connected to the spherical chamber wall is shown in FIG. 3, while FIGS. 5 and 6 show in more detail another solution. FIG. 3 shows the outer layer 13 of the door 6 fitted with locking catches 16 which interact with the locking catches 17 arranged on the outer layer of the sphere immediately around the opening 5. In an equivalent manner the door inner splinter protection layer 14 is connected to the sphere splinter protection layer 3 by means of locking catches 18 which interact with locking catches 19 which are attached to the sphere splinter protection layer 3. FIG. 3 also shows that the edge 20 which demarcates the wall opening 5 is only attached to the sphere splinter protection layer 3, and that there is a fine gap between this edge and the structural layer 2. As indicated by FIGS. 4-6 the door locking catches are arranged peripherally round the opening 5 at which the locking catches or locking grooves alternate with openings which enable the door catches on the door and frame to be entered beside each other after which, when locking, the door is turned around its own axis 21 where it is rotatably mounted on a hinged bracket 22 which in turn is swing mounted on the outer side of the sphere. The rotation of the door necessary for locking is equivalent to the width of one locking catch respectively the width of one opening between two locking catches. The example shown in FIGS. 4-6 is equivalent to a 10° rotation. Rotating is carried out with the aid of a rotatably mounted lever 23 whose point of leverage is between two of the tenons 24, 25 fixed on the outside of the sphere.

The locking mechanism is further developed in FIGS. 5 and 6 in as much as the outer and inner layers of the door are each fitted with double rows 26, 27 and 28, 29, of side-offset locking catches. The chamber outer and inner walls are furnished with an equivalent number of locking grooves 30-33. The locking grooves 30, 31 intended for the locking catches 26, 27 on the door splinter protection layer are formed as a coaming 34 which is connected to the chamber splinter protection layer 3, while the locking grooves 32, 33 intended for the locking catches 28, 29 on the structural outer layer 3 of the door are formed as an outer coaming 35 which in turn is connected to the outer structural layer 2 of the chamber wall. At the coaming fixation points there are reinforcement collars 36, 37. To safeguard the door outer, and inner layers relative to each other without at the same time causing a mechnacally operated vibration in phase between both layers in the event of a great rise in pressure in the chamber, safety bolts 38 which are fixed to one of the two layers but free of contact through an opening adapted for this reason in the other layer, and locked on the outside of the latter layer by means of a nut 39.

I claim:

1. An improved substantially spherical container or chamber for confining the increase in pressure and the fragments produced by explosion, deflagration or detonation of explosive substances, said container comprising:

an outer substantially spherical container shell dimensioned for absorbing said increase in pressure;
an inner, substantially spherical container shell dimensioned for withstanding said fragments;
first means, comprising a shock absorbent plastic layer positioned between said inner and outer container shells, for preventing rigid interconnection between said inner and outer container shells, there being no point of connection between said container shells which would force said inner container shell to vibrate in phase with said outer container shell and attain critical values;
at least one opening through said inner and outer shells and said layer; and
at least one door for said at least one opening, said door comprising:
an outer door shell also dimensioned for absorbing said increase in pressure;
an inner door shell also dimensioned for withstanding said fragments;
second means, comprising a shock absorbent plastic layer positioned between said inner and outer door shells, for preventing rigid interconnection between said inner and outer door shells, there being no point of connection between said door shells which would force said inner door shell to vibrate in phase with said outer door shell and attain critical values;
third means, extending between said at least one door and said outer container shell, for locking said outer door shell to said outer container shell; and
fourth means, extending between said at least one door and said inner container shell, for locking said inner door shell to said inner container shell while preventing said inner shells from vibrating in phase with said outer shells.

2. An improved substantially spherical container or chamber for confining the increase in pressure and the fragments produced by explosion, deflagration or detonation of explosive substances, said container comprising:

an outer substantially spherical container shell dimensioned for absorbing said increase in pressure;
an inner, substantially spherical container shell dimensioned for withstanding said fragments;
first means, comprising a shock absorbent plastic layer positioned between said inner and outer container shells and an open gap between said shells, for preventing a direct, rigid interconnection between said inner and outer container shells, there being no point of connection between said container shells which would force said inner container shell to vibrate in phase with said outer container shell and attain critical values;
at least one opening through said inner and outer shells and said layer; and
at least one door for said at least one opening, said door comprising:
an outer door shell also dimensioned for absorbing said increase in pressure;
an inner door shell also dimensioned for withstanding said fragments;
second means, comprising a shock absorbent plastic layer positioned between said inner and outer door shells and an open gap between said shells, for preventing a direct, rigid interconnection between said inner and outer door shells, there being no point of connection between said door shells which would force said inner door shell to vibrate in phase with said outer door shell and attain critical values;
third means, extending between said at least one door and said outer container shell, for locking said outer shell to said outer container shell; and
fourth means, extending between said at least one door and said inner container shell, for locking said inner door shell to said inner container shell while preventing said inner shells from vibrating in phase with said outer shells.

3. An improved substantially spherical container or chamber for confining the increase in pressure and the fragments produced by explosion, deflagration or detonation of explosive substances, said container comprising:

an outer substantially spherical container shell dimensioned for absorbing said increase in pressure;

an inner, substantially spherical container shell dimensioned for withstanding said fragments;

first means, comprising a shock absorbent plastic layer positioned between said inner and outer container shells, for preventing rigid interconnection between said inner and outer container shells, there being no point of connection between said container shells which would force said inner container shell to vibrate in phase with said outer container shell and attain critical values;

at least one circular opening through said inner and outer shells and said layer; and at least one circular door for said at least one circular opening, said circular door comprising:

a circular outer door shell also dimensioned for absorbing said increase in pressure;

a circular inner door shell also dimensioned for withstanding said fragments;

second means, comprising a shock absorbent plastic layer positioned between said inner and outer door shells, for preventing rigid interconnection between said inner and outer door shells, there being no connection between said door shells which would force said inner door shell to vibrate in phase with said outer door shell and attain critical values; and third means, extending between said at least one circular door and said inner and outer container shells, for locking said circular outer door shell to said outer container shells and said circular inner door shell to said inner container shell while preventing said inner shells from vibrating in phase with said outer shells, said third means comprising a first row of locking grooves arranged around the periphery of said circular opening at said inner container shells, said first row of locking grooves being separated by peripherally extending open spaces; a second row of locking grooves arranged around the periphery of said circular opening at said outer container shell, said second row of locking grooves also being separated by peripherally extending open spaces, there being no point of connection between said rows of grooves which would force said inner and outer container shells to vibrate in phase; a corresponding first row of locking catches arranged around the periphery of said at least one circular door at said circular inner door shell, said first row of locking catches being separated by further peripherally extending open spaces, a corresponding second row of locking catches arranged around the periphery of said at least one circular door at said circular outer door shell, said second row of locking catches also being separated by further peripherally extending open spaces, there being no point of connection between said rows of locking catches which would force said inner and outer door shells to vibrate in phase; means for positioning said at least one circular door within said at least one circular opening whereby said locking catches and said locking grooves are positioned beside each other; and means for rotating said circular door within said circular opening to cause said locking catches to engage said locking grooves.

4. An improved substantially spherical container or chamber for confining the increase in pressure and the fragments produced by explosion, deflagration or detonation of explosive substances, said container comprising:

an outer substantially spherical container shell dimensioned for absorbing said increase in pressure;

an inner, substantially spherical container shell dimensioned for withstanding said fragments;

first means, comprising a shock absorbent plastic layer positioned between said inner and outer shells, for preventing rigid interconnection between said inner and outer container shells, there being no point of connection between said container shells which would force said inner container shell to vibrate in phase with said outer container shell and attain critical values;

at least one circular opening through said inner and outer shells and said layer; and at least one circular door for said at least one opening, said circular door comprising:

a circular outer door shell also dimensioned for absorbing said increase in pressure:

a circular inner door shell also dimensioned for withstanding said fragments;

second means, comprising a shock absorbent plastic layer positioned between said inner and outer door shells, for preventing rigid interconnection between said inner and outer door shells, there being no point of connection between said container shells which would force said inner door shell to vibrate in phase with said outer door shell and attain critical values; and third means, extending between said at least one door and said inner and outer container shells, for locking said outer door shell to said outer container shell and said inner door shell to said inner container shell while preventing said inner shells from vibrating in phase with said outer shells said third means comprising a first double row of locking grooves arranged around the periphery of said circular opening at said inner container shell, said first double row of locking grooves being separated by peripherally extending open spaces; a second double row of locking grooves arranged around the periphery of said circular opening at said outer container shell, said second double row of locking grooves also being separated by peripherally extending open spaces, there being no point of connection between said rows of locking grooves which would force said inner and outer container shells to vibrate in phase; a corresponding first double row of locking catches arranged around the periphery of said at least one circular door at said circular inner door shell, said first double row of locking catches being separated by further peripherally extending open spaces; a second double row of locking catches arranged around the periphery of said at least one circular door at said circular outer door shell, said second double row of locking catches also being separated by further peripherally extending open spaces, there being no point of connection between said rows of locking catches which would force said inner and outer door shells to vibrate in phase; means for positioning said at least one circular door within said at least one circular opening whereby said locking catches and said locking grooves are positioned beside each other; said third means further comprising a hinge extending between said circular door and said outer container shell, said circular door being mounted to said hinge for rotation within said circular opening; and means for rotating said circular door within said circular opening to cause said locking catches to engage said locking grooves.

5. An improved chamber according to claim 4, wherein said locking catches at said outer door shell extend farther radially from the periphery of said door than said locking catches at said inner door shell.

* * * * *